United States Patent [19]

Uflacker et al.

[11] Patent Number: 5,524,635
[45] Date of Patent: Jun. 11, 1996

[54] APPARATUS FOR ADVANCING A GUIDE WIRE

[75] Inventors: Renan Uflacker, San Paulo, Brazil; Gary W. Gomringer, La Mesa, Calif.

[73] Assignee: Interventional Technologies Inc., San Diego, Calif.

[21] Appl. No.: 328,094

[22] Filed: Oct. 24, 1994

Related U.S. Application Data

[63] Continuation-in-part of Ser. No. 268,769, Jun. 29, 1994, Pat. No. 5,443,078, which is a continuation-in-part of Ser. No. 120,473, Sep. 13, 1993, abandoned, which is a continuation of Ser. No. 944,473, Sep. 14, 1992, Pat. No. 5,243,997.

[51] Int. Cl.⁶ .......................................... A61B 5/00
[52] U.S. Cl. .......................................... 128/772
[58] Field of Search .......................... 128/657, 658, 128/772, 32; 604/22

[56] References Cited

U.S. PATENT DOCUMENTS

| | | |
|---|---|---|
| 3,315,663 | 11/1967 | Goldfarb . |
| 3,589,363 | 6/1971 | Banko et al. . |
| 3,823,717 | 7/1974 | Pohlman et al. . |
| 3,900,023 | 8/1975 | McBride . |
| 4,504,264 | 3/1985 | Kelman . |
| 4,686,982 | 8/1987 | Nash . |
| 4,696,667 | 9/1987 | Masch . |
| 4,800,890 | 1/1989 | Cramer . |
| 4,844,092 | 7/1989 | Rydell et al. . |
| 4,854,325 | 8/1989 | Stevens . |
| 4,861,332 | 8/1989 | Parisi . |
| 4,898,575 | 2/1990 | Fischell et al. . |
| 4,957,117 | 9/1990 | Wysham . |
| 5,026,384 | 6/1991 | Farr et al. . |
| 5,161,534 | 11/1992 | Berthiaume . |

Primary Examiner—Max Hindenburg
Attorney, Agent, or Firm—Nydegger & Associates

[57] ABSTRACT

A hand held vibrating device which imparts a combination of transverse and longitudinal vibrations to a guide wire, to assist in advancing the guide wire through a blood vessel and through a stenosis in a blood vessel. The vibrating device contains a motor which drives a set of gears, rotating an eccentric pin. The rotation of the eccentric pin is translated to pivoting of an oscillating arm by the essentially longitudinal movement of a connector bar. The oscillating arm is attached to the guide wire by a releasable collet. Pivoting of the collet by the oscillating arm results in the introduction of a combination of transverse and longitudinal motion to the guide wire.

7 Claims, 2 Drawing Sheets

APPARATUS FOR ADVANCING A GUIDE WIRE

RELATED APPLICATIONS

This is a continuation-in-part application based upon U.S. application Ser. No. 08/268,769, filed Jun. 29, 1994, now U.S. Pat. No. 5,443,078, which was a continuation-in-part application based upon U.S. application Ser. No. 08/120,473, filed Sep. 13, 1993, now abandoned which was a continuation application based upon U.S. application Ser. No. 944,473, filed Sep. 14, 1992, now U.S. Pat. No. 5,243,997.

TECHNICAL FIELD

The present invention relates generally to angioplasty and atherectomy procedures for opening a stenotic segment of a blood vessel. The present invention is particularly, though not exclusively, useful for moving a guide wire through a stenosis so that an inflatable device or a cutter device can be positioned at the stenosis.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of arterial blockages reducing arterial blood flow. Consequently, several methods have been introduced to alleviate the effects of plaque build-up restricting the arterial lumen. One such method is a procedure termed angioplasty, which uses an inflatable device positioned in the artery to dilate the lumen at the stenosis. A typical angioplasty device is disclosed in U.S. Pat. No. 4,896,669 to Bhate et al. The angioplasty device of Bhate et al includes an inflatable balloon which is attached to the distal end of a hollow catheter. The proximal end of the catheter is attached to a fluid source, providing fluid communication between the balloon and the fluid source, To treat an arterial stenosis, a guide wire is first advanced through the artery past the stenosis. Then, a balloon such as the Bhate et al balloon is introduced into the artery in a deflated state and guided through the artery over the guide wire to a position adjacent the stenosis. Fluid from the fluid source is then infused into the balloon via the catheter to inflate the balloon. As the balloon expands, it dilates the lumen of the artery. The balloon is then deflated and removed from the artery.

While effective for dilating the lumen at the stenosis, angioplasty devices, such as the Bhate et al device, do not remove the plaque from the artery. Consequently, the residual plaque either remains in place at the point of the stenosis or breaks off and migrates to other locations in the blood stream. In either case the plaque remains a continuing threat to create blockages in the circulatory system. To address the shortcomings of angioplasty, a procedure termed atherectomy has been devised which cuts and removes the plaque comprising the stenosis from the blood vessel.

An atherectomy procedure typically includes inserting a guide wire into the affected artery and advancing a hollow cutting device over the wire until the cutting device is positioned adjacent the stenosis. The cutting device is then advanced into the stenosis to cut a channel through the plaque, thereby increasing blood flow through the artery. The resulting plaque fragments are removed from the blood stream by drawing them into the hollow cutting device.

A number of atherectomy devices capable of performing this procedure are known in the art. U.S. Pat. No. 4,895,166 to Farr et al, which is assigned to the same assignee as the present invention, discloses an atherectomy device having a frustum-shaped cutter which is attached to the distal end of a hollow catheter. The cutter has two openings that define two straight, even cutting blades. The cutter is directed through the artery over a guide wire, and it is rotated as it advances into the stenosis, thereby cutting the plaque. Excised plaque enters the openings of the cutter and is subsequently removed through the hollow catheter.

A particular problem associated with angioplasty and atherectomy procedures is in moving the guide wire through the stenosis so that an inflatable balloon or cutting device can be positioned within or adjacent to the stenosis. A stenotic segment of a blood vessel presents a narrowed and often tortuous path through which the guide wire must be advanced. In some cases the stenotic segment of the blood vessel may be almost completely blocked (i.e. occluded) with atherosclerotic plaque. If the distal end of the guide wire contacts the stenosis at a location where there is no opening, the guide wire distal end must be moved laterally to find an opening, or an opening must be created. Some currently known systems oscillate or vibrate the guide wire longitudinally to cause the distal end of the wire to create an opening with a kind of picking action. The success of this maneuver depends upon the wire being stiff enough to penetrate the stenotic material. The longitudinal oscillations are not very efficient at moving the distal end of the guide wire laterally to seek out an existing opening.

In addition, as the guide wire passes through the blood vessels, it must pass through numerous turns and curves. At each turn, or even at a slight curve, the guide wire lies in direct contact, over an appreciable extent of its length, with the blood vessel wall. Indeed, the guide wire is in direct contact with the blood vessel wall over a significant part of its inserted length, and the force of contact with the wall is increased at turns and curves. This contact also occurs between the side of the wire and the stenotic material as the distal portion of the wire passes through the stenosis. Once the wire begins passing through the blood vessel, contacting the wall at a given location, it tends to remain in continual contact with the wall at that location, during most of the period of time while wire insertion is being accomplished. Therefore, as the physician advances the guide wire through the blood vessel, it drags on the vessel walls, over much of its inserted length, and this drag is experienced essentially continually during the wire insertion procedure. This means that every minute increment of advancement attempted by the physician is resisted by frictional drag over much of the length of inserted wire. This drag, resulting from friction between the wire and the wall or between the wire and the stenosis, is a significant contributor to the difficulty in advancing the guide wire through the blood vessel, and ultimately through the stenosis.

Systems which attempt to assist in advancing the guide wire by vibrating or oscillating the wire longitudinally do not alleviate the frictional drag problem, because the longitudinal vibrations or oscillations of the wire do not reduce the physical extent of contact between the wire and the wall, and they do not reduce the time of contact between the wire and the wall. At best, the longitudinal vibrations create a continual sliding contact between the wire and the vessel wall. Accordingly, the present invention recognizes the need, in the treatment of an occluded or narrowed blood vessel, for a method of lessening the frictional drag on the blood vessel wall to assist in moving a guide wire easily through the blood vessel. The present invention also recognizes the possibility of reducing this frictional drag by reducing the physical extent of contact between the guide wire and the vessel wall, and by reducing the time of contact between the wire and the wall. Both the physical extent of contact and the time of contact are reduced by introducing transverse vibrations into the guide wire.

It is therefore an object of the present invention to provide an apparatus for advancing a guide wire which transversely and longitudinally vibrates the guide wire such that the guide wire can be more easily moved through a blood vessel and through a stenotic segment of a blood vessel. It is another object of the present invention to provide an apparatus that is especially adapted for use in angioplasty and atherectomy medical procedures. It is a further object of the present invention to provide an apparatus for advancing a guide wire that is relatively easy and cost effective to manufacture.

SUMMARY OF THE INVENTION

In accordance with the present invention, a novel apparatus is provided for use with a guide wire for angioplasty and atherectomy procedures. The apparatus is used in a process which, simply stated, begins with introduction of the guide wire into the blood vessel by well known surgical techniques, followed by advancement through the blood vessel to the stenotic segment. During advancement, the vibrating device of the present invention can be used to hold and vibrate the guide wire with a combined longitudinal and transverse action to create a sinusoidal wave in the longitudinally vibrating wire, so that it may be more easily pushed through the blood vessel and through the stenotic segment. The sinusoidal wave can be a traveling wave or a standing wave, depending upon the flexural modulus of the guide wire, the frequency of the vibration, and the damping effect of the catheter and blood vessel through which the guide wire passes, as well as the damping effect of the fluid in the vessel.

The vibrating device is adapted to be hand held by the physician or other medical personnel during the medical procedure. It consists of an oscillatory motion source attached to a collet through which the guide wire passes. The collet is mounted on an oscillator arm which vibrates or oscillates with a pivoting action, causing the collet to pivot about an axis which is offset from, but substantially orthogonal to, the longitudinal axis of the wire. The source of the oscillatory pivoting motion is capable of being selectively energized for intermittent operation as required. In use, the guide wire can be releasably placed within the collet and repositioned or advanced through the collet as the guide wire is vibrated and pushed through the stenosis.

The novel features of this invention will be best understood from the accompanying drawings, taken in conjunction with the accompanying description, in which similar reference characters refer to similar parts.

DETAILED DESCRIPTION

Figure 1:
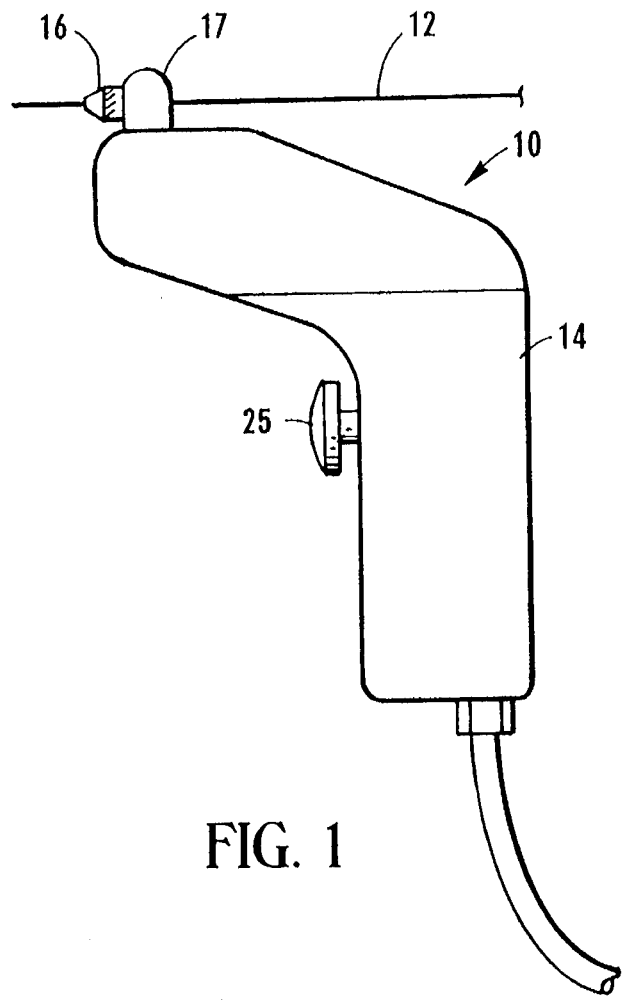
FIG. 1 is a side elevation view of the vibrating device of the present invention.
Figure 2:
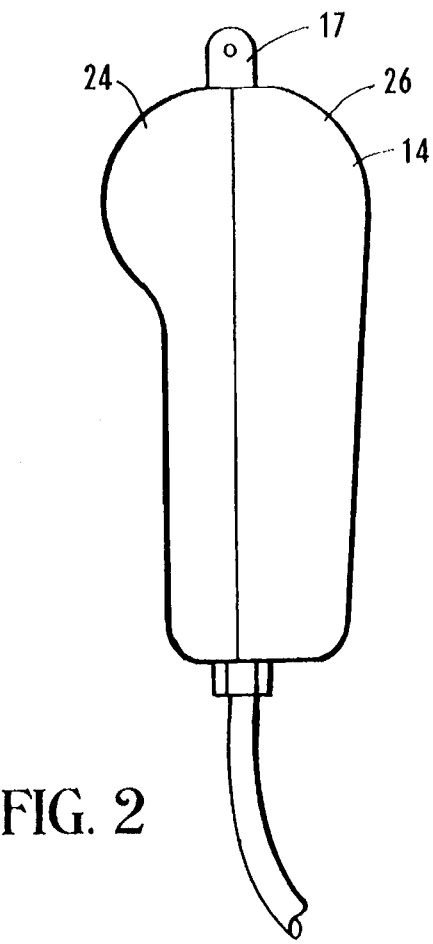
FIG. 2 is a rear elevation view of the vibrating device shown in FIG. 1.
Figure 3:
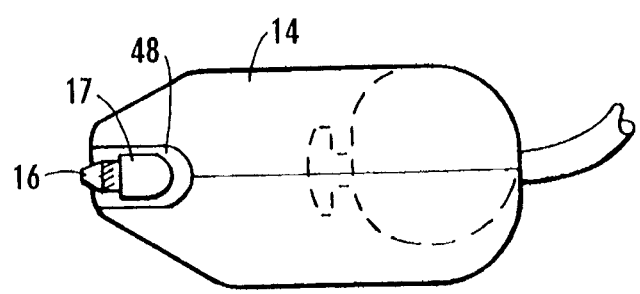
FIG. 3 is a top view of the vibrating device shown in FIG. 1.
Figure 4:
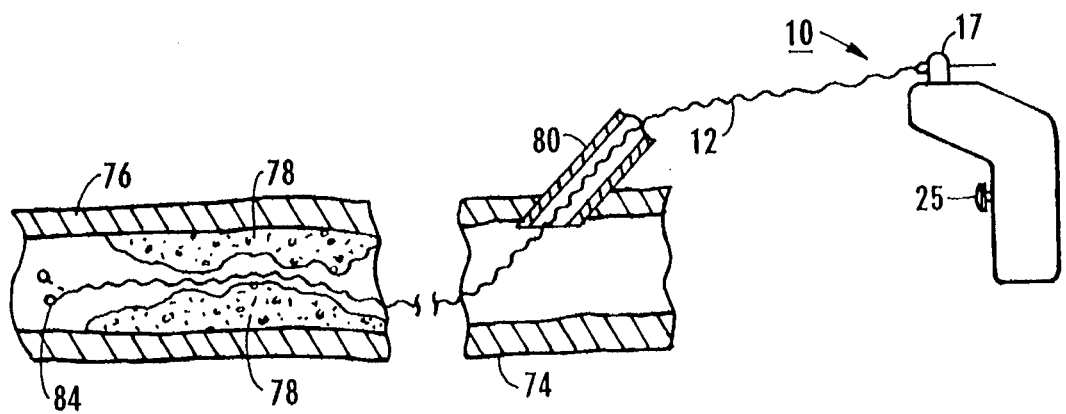
FIG. 4 is an enlarged schematic cross sectional view of a stenotic segment of a blood vessel showing a vibrating guide wire being pushed through a stenotic segment of a blood vessel.

Referring to FIGS. 1, 2 and 3, the vibrating device of the present invention is shown and generally designated as 10. The device 10 achieves the combined longitudinal and transverse vibration of the guide wire 12 that is useful in advancing the guide wire 12. The illustrated device 10 is powered by an air motor, but other types of power, such as electrical power, could be used to operate the device 10. The vibrating device 10 is adapted to hold and vibrate an elongated flexible guide wire 12 which can be used in a medical procedure such as an angioplasty or atherectomy procedure as previously described, in which the guide wire 12 is pushed through a stenotic segment of a blood vessel, as seen in FIG. 4. Use of the vibrating device 10 is not restricted to a solid guide wire 12, however, as it may be utilized to move other medical devices, such as a hollow wire or an elongated flexible catheter, through a blood vessel.

Figure 5:
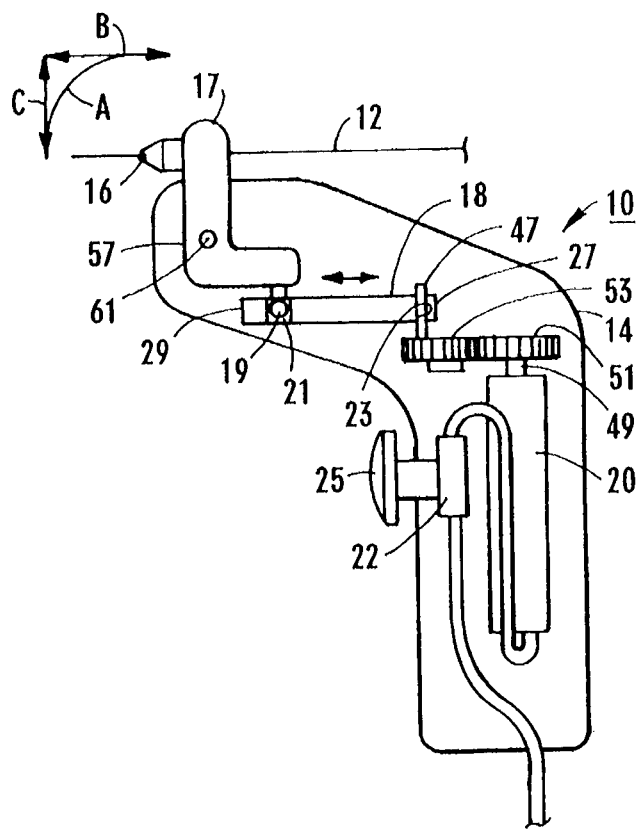
FIG. 5 is a breakaway view of the vibrating device of FIG. 1, showing mechanical coupling between the collet and the air motor.

Also referring to FIG. 5, the vibrating device 10 includes a case 14, holding means in the form of a collet member 16, mounted on an oscillating arm 17 which is pivotally mounted to the case 14, for releasably holding the guide wire 12. The oscillating arm 17 is connected by means of a connector bar 18 to an air motor 20, which is controlled by a control valve 22. This mechanism vibrates the oscillating arm 17, the collet 16, and the guide wire 12 positioned within the collet 16.

The case 14 is adapted to be hand held by the physician while the guide wire 12 is pushed through the blood vessel. The case 14 is sized and shaped to fit easily in a person's hand while the guide wire 12 and the collet 16 are manipulated with the other hand. The case 14 has a pistol grip configuration and is formed in two mating halves. The case 14 may be formed of a sturdy, cleanable, material such as molded plastic.

As seen in FIGS. 2 and 3, the case 14 can include a left portion 24 and a mating right portion 26. FIG. 5 illustrates the mechanical coupling of the collet 16 to the air motor 20. The output shaft 49 of the air motor 20 turns a first gear 51 which meshes with a second gear 53. The second gear 53 turns an eccentric pin 47 which travels in an orbital motion. This imparts an essentially circular motion to a first end 27 of the connector bar 18. The connector bar 18 can be constrained to travel in a planar path perpendicular to the rotational axis of the second gear 53. A second end 29 of the connector bar is attached to the lower end of the oscillating arm 17. This causes the oscillating arm 17 to pivot, which imparts a vibratory transverse and longitudinal motion to a guide wire 12 secured to the oscillating arm 17 by the collet 16.

The oscillating arm 17 is pivotally mounted within the housing 14 for rapid pivotal oscillatory or vibratory motion. A pivot pin 57 projects transversely through the oscillating arm 17, establishing a pivot axis 61 for the oscillating arm 17. The pivot axis 61 is aligned substantially orthogonal to, but offset from, the guide wire 12. A slot 48 is located in the housing 14 for allowing the oscillating arm 17 to move pivotably. The center of the pivot radius of the collet 16 is on the pivot axis 61. The slot 48 is dimensioned to be slightly larger than the oscillating arm 17, such that the oscillating arm 17 has a range of pivotal motion within the slot 48.

The oscillating arm 17 is coupled to the connector bar 18 by means of the pawl 19 on the lower end of the oscillating arm 17, with the pawl 19 being captured within a socket 21 on one end of the connector bar 18. If the connector bar 18 is not constrained to move in a single plane, it can alternatively be constrained by its attachment to the pawl 19. The other end of the connector bar 18 has a hole 23 which receives the eccentric pin 47. The eccentric pin 47 has an orbital motion with a radius equal to the distance from the eccentric pin 47 to the rotational axis of the second gear 53. The eccentric pin 47 extends from the face of the second gear 53, parallel to the rotational axis of the second gear 53. The range of motion of the oscillating arm 17 is slightly less than the length of the slot 48. The oscillating arm 17 is thus free to pivot first in one direction, and then in the other direction, along the slot 48.

In operation of the vibrating device 10, the trigger button 25 is pressed to open the control valve 22, applying air pressure to the air motor 20 to cause it to turn. Pressing the trigger button 25 farther inwardly causes the control valve 22 to open farther, in turn causing the air motor 20 to run faster. The air motor 20 turns the first gear 51 at the desired speed, which causes the second gear 53 to turn. The relative diameters of the gears 51, 53 can be designed to achieve the desired rotational speed which will result in the desired range of vibratory frequency of the guide wire 12. For best results, the device 10 must achieve a vibratory frequency at the collet of at least 125 Hz.

As the second gear 53 rotates, this also rotates the eccentric pin 47 in an orbital path. The eccentric pin 47 fits into the hole 23 in a first end 27 of the connector bar 18. As the eccentric pin 47 orbits, the first end 27 of the connector bar 18 also orbits in a circular path, causing a second end 29 of the connector bar 18 to follow. The second end 29 of the connector bar 18 is attached to the lower end of the oscillating arm 17 by means of the pawl 19 being captured within the socket 21. The oscillating arm 17 is constrained by the housing 14 to pivot in a planar path perpendicular to the pivot axis 61. This constrains the pawl 19 to move only in the same plane, which in turn constrains the socket 21 to vibrate only in a longitudinal path. The placement of the eccentric pin 47 on the second gear 53 can be designed, in conjunction with the configuration of the oscillating arm 17, to achieve the desired amplitude of longitudinal and transverse vibrations of the guide wire 12.

Therefore, the oscillating arm 17 is driven to oscillate along the slot 48 by the air motor 20. This provides the pivotal vibratory motion which then is imparted to the guide wire 12 as a combination longitudinal and transverse action. The pivotal vibratory motion of the collet 16 is confined to a single plane perpendicular to the pivot axis 61, as the collet 16 is free to move in only a single plane as it rotates about the pivot axis 61. The vibrating action of the guide wire 12 at the collet 16 will be in the same plane as the vibratory motion of the collet 16, but farther down the guide wire 12, the vibrating motion can occur in any plane or in a constantly changing plane, at any given point.

Unlike the collet 16, which is free to vibrate in only a single plane, the guide wire 12 within the blood vessel will vibrate in three dimensions. Regardless of the plane in which the guide wire 12 vibrates at any given location, the direction of the vibration, represented by the vector A, will be a combination of transverse and longitudinal motion, resulting in a whip like action, to facilitate advancement through the blood vessel or through a stenosis. The desired ratio between the longitudinal component, represented by the vector B, and the transverse component, represented by the vector C, can be achieved by appropriate configuration of the angle of the oscillating arm 17. A relatively greater longitudinal component will result in greater penetrating ability, while a relatively greater transverse component will result in less frictional drag.

Referring now to FIG. 4, the vibrating device 10 is shown being used in advancing a guide wire. A blood vessel such as an artery 74 includes a stenotic segment 76 wherein a build up of atherosclerotic plaque 78 is located. In order to perform an angioplasty or atherectomy procedure, a guide wire 12 must be advanced along the blood vessel and pushed through the stenotic segment 76 to locate an inflatable balloon or cutter device within the stenotic segment 76. Initially, the guide wire 12 is placed into the artery 74 utilizing an introductory catheter 80 that is percutaneously inserted into the artery 74. The guide wire 12 can then be directed through the artery 74 to the stenotic segment 76 of the artery 74, utilizing well known techniques such as radiological tracking. The guide wire 12 may in fact be formed with a radiopaque tip 84 at its distal end to facilitate such a procedure.

A portion of the guide wire 12 can be clamped within the collet 16 of the vibrating device 10, so that the guide wire 12 can be vibrated and pushed along the blood vessel and through the stenotic segment 76 of the artery 74. As the guide wire 12 vibrates transversely, the extent of contact between the wire 12 and the artery wall is significantly reduced, with contact only occurring at essentially the crests of the sinusoidal waves. The great preponderance of the length of the wire is between the crests at any point in time, so the extent of contact between the wire and the vessel wall is dramatically reduced. The time of contact is also significantly reduced, with each contact between the wire and the vessel wall lasting only for an instant of time. Therefore, any given point on the wire is subject to contact with the wall for only a very short time, as compared to the long time between contacts, when the given point is free from contact. Any incremental advancement of the wire during the free time between contacts is completely free from frictional drag, at the given point. These reductions of the extent of contact and the time of contact result in a significant reduction in the frictional drag as the wire is advanced through the blood vessel.

The build up of plaque 78 in the artery 74 would normally make it difficult to pass the guide wire 12 through the stenotic segment 76. By selectively actuating the air motor 20 to vibrate the guide wire 12, however, the physician is more easily able to direct the guide wire 12 through the plaque 78. The end of the vibrating guide wire 12 in effect moves laterally and longitudinally to find an open channel through the plaque 78, or alternatively the combined longitudinal and transverse motion of the wire end cuts its own path through the plaque. This can result, at least partially, from a whipping of the distal end of the guide wire 12.

The collet 16 of the vibrating device 10 can be used to hold the guide wire 12 while it is advanced through the blood vessel or the stenotic segment and to alternately grip and release the guide wire 12 while the proximal end of the guide wire 12 is relocated with respect to the vibrating device 10. During this procedure, the vibrating device 10 is held in the physician's hand. The physician operates the trigger button 25, which controls the air motor 20, and manipulates the guide wire 12 and the collet as required.

Thus the apparatus of the present invention facilitates an effective method for advancing a wire, particularly suited to angioplasty and atherectomy procedures. While the particular apparatus for advancing a guide wire as herein shown and disclosed in detail is capable of obtaining the objects and providing the advantages hereinbefore stated, it is understood that this particular embodiment is merely illustrative of the present invention. It is further understood that the present invention is not intended to be so limited, and that other variations of this apparatus are further possible within the scope of the present invention.

We claim:

1. A guide wire vibrating apparatus, comprising:
   a housing;
   a motor mounted within said housing;
   an eccentric pin drivably connected to said motor for orbital travel in a circular path;
   a connector bar having a first end and a second end, said first end being attached to said eccentric pin for orbital travel with said eccentric pin;
   an oscillating arm pivotably mounted to said housing, said oscillating arm having a first end and a second end, said first end being drivably connected to said second end of said connector bar, for pivotally oscillating said oscillating arm; and
   a guide wire attachment means mounted on said oscillating arm for releasably attaching the guide wire to said second end of said oscillating arm, for introducing transverse and longitudinal vibrations into the guide wire.

2. A guide wire vibrating apparatus, as claimed in claim 1, further comprising:
   a plurality of drive gears drivably connecting said motor to said eccentric pin;
   a hole in said first end of said connector bar to receive said eccentric pin to drivably attach said first end of said connector bar to said eccentric pin;
   a socket in said second end of said connector bar; and
   a pawl on said first end of said oscillating arm, said pawl mating with said socket to drivably connect said second end of said connector bar to said first end of said oscillating arm.

3. A guide wire vibrating apparatus, as claimed in claim 1, further comprising a pivot pin mounted to said housing for pivotably connecting said oscillating arm to said housing, wherein said pivot pin establishes a pivot axis for said oscillating arm, said pivot axis being substantially orthogonal to the longitudinal axis of the guide wire.

4. A guide wire vibrating apparatus, as claimed in claim 1, further comprising:
   a speed control mounted in said housing for selectively controlling the speed of said motor; and
   a trigger button attached to said control for selectively operating said control to control the speed of said motor.

5. A guide wire vibrating apparatus, as claimed in claim 1, further comprising a releasable collet mounted on said second end of said oscillating arm for selectively gripping the guide wire.

6. A guide wire vibrating apparatus, comprising:
   a pistol grip housing;
   a variable speed motor mounted within said housing, said motor having a rotating drive shaft;
   an adjustable control for selectively controlling the speed of said motor;
   a first drive gear drivably connected to said drive shaft of said motor;
   a second drive gear drivably connected to said first drive gear;
   an eccentric pin mounted on said second drive gear for travel in an orbital path about the axis of rotation of said second drive gear, said eccentric pin having a longitudinal axis parallel to said axis of rotation of said second drive gear;
   a connector bar having a first end and a second end, said first end being attached to said eccentric pin for orbital travel with said eccentric pin;
   a socket formed in said second end of said connector bar;
   a pivot pin mounted to said housing;
   an oscillating arm pivotably mounted to said pivot pin, said oscillating arm having a first end and a second end;
   a pawl mounted on said first end of said oscillating arm, said pawl mating with said socket for drivably connecting said first end of said oscillating arm to said second end of said connector bar, for pivotally oscillating said oscillating arm; and
   a releasable collet mounted on said oscillating arm for releasably attaching the guide wire to said second end of said oscillating arm, for introducing transverse and longitudinal vibrations into the guide wire.

7. A method for introducing transverse and longitudinal vibrations into a guide wire, comprising the steps of:
   providing a hand held vibratory device having an adjustable speed motor, a set of drive gears connected to said motor, an eccentric pin mounted on one of said gears, a connector bar attached to said eccentric pin, an oscillating arm connected to said connector bar, and a collet mounted on said oscillating arm;
   attaching the guide wire to said oscillating arm by gripping the guide wire with said collet;
   selectively regulating the speed of said air motor to cause the drive shaft of said motor to rotate at a desired speed;
   translating said rotational motion of said motor drive shaft to orbital motion of said eccentric pin about an axis parallel to the longitudinal axis of said eccentric pin, by rotation of said drive gears;
   translating said orbital motion of said eccentric pin to oscillating pivotal motion of said oscillating arm by means of said connector bar; and
   introducing transverse and longitudinal vibratory motion into the guide wire by oscillating movement of said collet.

\* \* \* \* \*